(12) United States Patent
Tominaga et al.

(10) Patent No.: US 8,959,669 B2
(45) Date of Patent: Feb. 24, 2015

(54) GOGGLES

(75) Inventors: Hirofumi Tominaga, Osaka (JP); Shinichi Hadehara, Osaka (JP)

(73) Assignee: Yamamoto Kogaku Co. Ltd., Osaka (JP)

( * ) Notice: Subject to any disclaimer, the term of this patent is extended or adjusted under 35 U.S.C. 154(b) by 908 days.

(21) Appl. No.: 12/661,294

(22) Filed: Mar. 15, 2010

(65) Prior Publication Data
US 2010/0229291 A1  Sep. 16, 2010

(30) Foreign Application Priority Data

Mar. 13, 2009  (JP) ................. 2009-061422

(51) Int. Cl.
*A61G 9/02*  (2006.01)
*A61F 9/02*  (2006.01)

(52) U.S. Cl.
CPC ............. *A61F 9/027* (2013.01); *A61F 9/025* (2013.01)
USPC .................................................. 2/431; 2/448

(58) Field of Classification Search
USPC .............................. 2/431, 429, 441, 446, 450
See application file for complete search history.

(56) References Cited

U.S. PATENT DOCUMENTS

| | | | | | |
|---|---|---|---|---|---|
| 5,387,949 | A | * | 2/1995 | Tackles ............. | 351/121 |
| 5,410,763 | A | * | 5/1995 | Bolle .................. | 2/436 |
| 5,706,527 | A | * | 1/1998 | Kita et al. .......... | 2/452 |
| 5,802,622 | A | * | 9/1998 | Baharad et al. .... | 2/434 |
| 6,105,177 | A | * | 8/2000 | Paulson et al. .... | 2/431 |
| 6,513,170 | B1 | * | 2/2003 | Chiang .............. | 2/428 |
| 6,742,891 | B2 | * | 6/2004 | Chen ................. | 351/140 |
| 6,832,394 | B1 | * | 12/2004 | Chiang .............. | 2/428 |
| 6,948,813 | B2 | * | 9/2005 | Parks ................. | 351/158 |
| 7,020,905 | B2 | * | 4/2006 | Chiang .............. | 2/448 |
| 7,257,848 | B2 | * | 8/2007 | Chiang .............. | 2/448 |
| 7,340,804 | B2 | * | 3/2008 | Saderholm et al. | 24/265 BC |
| 7,343,631 | B2 | * | 3/2008 | Lin .................... | 2/448 |
| 7,458,134 | B2 | * | 12/2008 | Shiue ................ | 24/68 E |

(Continued)

FOREIGN PATENT DOCUMENTS

| EP | 1 970 028 A1 | 9/2008 |
|---|---|---|
| EP | 2008625 A1 | 12/2008 |

(Continued)

OTHER PUBLICATIONS

Office Action issued in corresponding Chinese Application No. 201010135763.9 dated Nov. 14, 2012 with English translation.

(Continued)

*Primary Examiner* — Richale Quinn
(74) *Attorney, Agent, or Firm* — Heslin Rothenberg Farley & Mesiti P.C.

(57) ABSTRACT

Goggles include a frame, a lens and a pair of left and right belt arms. On the frame a first stop hole is provided each left and right of a middle of each of an upper frame and a lower frame of the frame. The lens has an upper side and a lower side each of which is provided with a second stop hole at a position corresponding to each first stop hole in the frame. Each of the pair of left and right belt arms has bifurcated portions, and each end of the bifurcated portions is provided with a lock mechanism. The frame and the lens are placed on each other and the respective first and second stop holes are aligned. By the mechanisms of the belt arms, the first and second stop holes are brought into either a lock state to secure the frame, the lens and the pair of left and right belt arms, or an unlock state where the lock state is released to separate them.

7 Claims, 24 Drawing Sheets

(56) References Cited

U.S. PATENT DOCUMENTS

| | | | |
|---|---|---|---|
| 7,640,633 B2* | 1/2010 | Chou | 24/68 E |
| 8,171,572 B2* | 5/2012 | Borsa et al. | 2/452 |
| 8,235,523 B2* | 8/2012 | Yang | 351/43 |
| 8,316,470 B2* | 11/2012 | McNeal et al. | 2/438 |
| 8,668,330 B2* | 3/2014 | Reyes et al. | 351/106 |
| 2003/0101507 A1 | 6/2003 | Cleary et al. | |
| 2004/0139532 A1* | 7/2004 | Parks | 2/431 |
| 2007/0234526 A1 | 10/2007 | Chen | |
| 2008/0134417 A1 | 6/2008 | Aoyama | |
| 2008/0137028 A1* | 6/2008 | Webb | 351/106 |
| 2008/0155736 A1 | 7/2008 | Paulson et al. | |
| 2008/0196149 A1* | 8/2008 | Takeshi et al. | 2/425 |
| 2008/0256688 A1* | 10/2008 | Bruce | 2/441 |
| 2009/0313746 A1* | 12/2009 | Wang | 2/431 |
| 2011/0023217 A1* | 2/2011 | Matera | 2/439 |

FOREIGN PATENT DOCUMENTS

| | | |
|---|---|---|
| JP | 50-29592 | 9/1975 |
| JP | 60122123 U | 8/1985 |
| JP | 61-160422 | 10/1986 |
| JP | 10-229998 | 9/1998 |
| JP | 2008200265 A | 9/2008 |
| TW | M300528 U | 11/2006 |

OTHER PUBLICATIONS

Office Action issued in corresponding Japanese Application No. 2009-061422 dated Mar. 6, 2013.

Office Action issued in corresponding Chinese Application No. 2009-061422 dated Mar. 6, 2013.

* cited by examiner

GOGGLES

CROSS REFERENCE TO RELATED APPLICATIONS

This application claims priority of Japanese Application No. 2009-61422 filed on Mar. 13, 2009, the entire contents of which are hereby incorporated herein by reference.

BACKGROUND OF THE INVENTION

1. Field of the Invention

The present invention relates to goggles applicable to snow goggles used for skiing, snowboarding or snow shoveling, motor sport goggles for riding bikes or buggies, water sport goggles for canoeing yachting, or surfing, or dustproof goggles used in factories or the like, and more particularly to goggles, as sport goggles, suitably used for doing sports that require a helmet.

2. Description of the Related Art

Conventional goggles include, for example, a single lens 32 removably mounted to a frame body 31 as shown in FIG. 12. In the goggles, the frame body 31 has a lens fitting peripheral portion, each of upper and lower portions thereof has an engaging protrusion 35 that engages an engaging portion 34 of the single lens 32.

Further, in the goggles, a rear end of the frame body 31 includes a protruding portion 37 having a passing hole 36 for a fitting belt (Japanese Patent Publication No. 50-29592).

As a conventional lens mounting structure, for example, as shown in FIG. 13, a bridge 41 has a through hole 42 passing through from a front surface to a back surface of the bridge 41, and a lens 43 having left and right parts as one unit has a notch 45 in a portion that abuts against the bridge 41 when fitted in a rim 44. A pin 46 is passed through the notch 45 in the lens 43 and the through hole 42 in the bridge 41 so as to secure the lens 43 to the rim 44. The pin 46 has a retainer plate 46a that retains a portion around the notch 45 in the lens 43, and the rim 44 has a pawl 47 in a portion against which each of left and right ends of the lens 43 abuts.

When the lens 43 is secured to the rim 44 in the lens mounting structure, the lens 43 is held among the pawls 47 and a groove 48 and abutted against the rim 44, and the notch 45 in the lens 43 is aligned with the through hole 42 in the bridge 41. Then, a shaft 46b of the pin 46 is inserted therethrough to cause an engaging portion 46c to protrude out from a back side of the through hole 42. Further, the pin 46 is rotated around the axis of the shaft 46b, and the engaging portion 46c is engaged with an edge of the through hole 42 on the back surface of the bridge 41 so as to secure the lens 43 to the rim 44.

In the lens mounting structure, belt holes 49 are provided in opposite ends of the rim 44, and a fitting belt (not shown) is put through the belt holes 49 (Japanese Utility Model Laid-Open No. 61-160422).

Further, other conventional goggles suitably used for doing sports that require a helmet, for example, as shown in FIG. 14, have a lens holding frame 51 and arms 52. The lens holding frame 51 has a front surface of an upper frame portion 51a and a front surface of a lower frame portion 51b, each of which has protruding positions in left and right portions. From the respective protruding positions, the arms 52 protrude out. The arms, made of soft elastic synthetic resin, and the frame portions 51a and 51b are formed as one unit. Each of the arms 52 has its end near a belt mounting position apart from the protruding position, and is connected to a belt 53 near the end through a belt mounting portion. The arm 52 is also designed to extend overlapping or substantially along the front surfaces of the upper and lower frame portions 51a and 51b of the lens holding frame 51. Further, the lens holding frame 51 has, in an inner surface thereof, a fitting groove 55 for fitting and holding the lens 54 so that the lens 54 fitted in the fitting groove 55 is not accidentally removed therefrom (Japanese Patent Laid-Open No. 10-229998, which corresponds to U.S. Pat. No. 6,076,196).

In the goggles shown in FIG. 12, the single lens 32 is mounted to the frame body 31 by engaging the engaging portion 34 of the single lens 32 with the engaging protrusion 35 provided on each of the upper and lower portions of the lens fitting peripheral portion 33 of the frame body 31. However, for a wearer who has gloves on and could use his or her thumbs and fingers less freely, it is difficult to engage them and it takes time to replace the single lens 32.

Further, in the conventional goggles shown in FIG. 12, when the wearer who has gloves on engages the lens 32 with the frame body 31, the gloves are likely to touch the single lens 32 and scrub against the surface of the single lens 32. Therefore, the single lens 32 is likely to be scratched in replacement.

Also, in the conventional goggles shown in FIG. 12, the fitting belt is merely put through the passing hole 36 in the protruding portions 37 simply provided at the rear ends of the frame body 31. Thus, in case a wearer wears a helmet, when the goggles are also put on, the fitting belt is pushed outward by a thickness of the helmet, and the frame body 31 rises apart from the wearer's face to lose the tight contact with the wearer's face.

Next, in the conventional lens mounting structure shown in FIG. 13, the lens 43 is held among the pawls 47 and the groove 48 and abutted against the rim 44. The notch 45 in the lens 43 is aligned with the through hole 42 in the bridge 41, and the pin 46 is passed through the through hole 42 in the bridge 41 and the notch 45 in the lens 43 to secure the lens 43 to the rim 44. Thus, the lens 43 can be easily mounted to the rim 44, but securing strength therebetween is weak, and a strong impact, if applied, may remove the lens 43 from the rim 44.

In the conventional lens mounting structure shown in FIG. 13, when a wearer's hand or any other object touches the retainer plate 46a of the pin 46 which protrudes on the front surface of the lens 43, the retainer plate 46a may be easily rotated and the engagement between the through hole 42 and the engaging portion 46c may be lost to cause unwanted removal of the lens 43 from the rim 44.

Further, in the conventional lens mounting structure shown in FIG. 13, the fitting belt is merely put through the belt holes 49 simply provided in the opposite ends of the rim 44. Thus, in case a wearer wears a helmet, when the goggles are also put on, the fitting belt is pushed outward by a thickness of the helmet, and the rim 44 rises apart from the wearer's face to lose the tight contact with the wearer's face.

In the conventional goggles shown in FIG. 14, the protruding arms 52, made of soft elastic synthetic resin, are formed with the upper frame portion 51a and the lower frame portion 51b as one unit. Thus, the fitting belt is not pushed outward by a thickness of the helmet, the lens holding frame 51 does not rise apart from a wearer's face, the tight contact between the frame 51 and the wearer's face is maintained. Consequently, the goggles are suitable for use for sports that requires a helmet. However, the fitting groove 55 formed in the inner surface of the lens holding frame 51 fits and holds the lens 54 so as to prevent the lens 54 from accidental removal but replacement of lenses is not possible in the goggles. Thus, the lens cannot be replaced with a lens having optimum visibility performance according to changes in the natural environment due to the intensity of the sun, snowfall or rainfall.

It is therefore an object of the present invention to solve the conventional problems as stated above, and provide goggles in which a lens is prevented from being inadvertently removed, able to be replaced, prevented from being readily touched with a wearer's hand in replacement, and the goggles is suitable for doing sports that require a helmet.

SUMMARY OF THE INVENTION

To achieve the object, goggles according to the present invention include a frame on which a respective first stop hole of a plurality of first stop holes is provided left and right of a middle of each of an upper frame member and a lower frame member of the frame; a lens having an upper side and a lower side on each of which a respective second stop hole of a plurality of second stop holes is provided at a position corresponding to a respective first stop hole in the frame; and a pair of left and right belt arms each having bifurcated portions, on each end of which a lock mechanism is provided. The frame and the lens are placed on each other and the respective first and second stop holes are aligned. The respective first and second stop holes can be brought either into a lock state by the lock mechanisms of the belt arms to secure the frame, the lens, and the pair of left and right belt arms, or into an unlock state by the lock mechanisms where the lock state is released to separate the frame, the lens, and the pair of left and right belt arms.

Goggles according to the present invention also include a frame on which a respective first stop hole is provided left and right of a middle of one of an upper frame member and a lower frame member of the frame; a lens having an upper side and a lower side on one of which a respective second stop hole is provided at a position corresponding to each respective first stop hole in the frame; and a pair of left and right belt arms each having bifurcated portions, on one end of which a lock mechanism is provided. The frame and the lens are placed on each other and the respective first and second stop holes are aligned. The respective first and second stop holes can be brought into either a lock state by the lock mechanisms of the belt arms to secure the frame, the lens, and the pair of left and right belt arms, or an unlock state by the lock mechanisms where the lock state is released to separate them.

In the goggles of the present invention, the other of the bifurcated portions may be coupled to one of the upper frame and the lower frame of the frame.

Further, in the goggles of the present invention, a groove may be provided in the other of the upper frame and the lower frame, and an upper edge or a lower edge of the lens is fitted into the groove.

Goggles according to the present invention further include a frame on which a respective first stop hole is provided left and right of a middle of each of an upper frame member and a lower frame member and on right and left side frames of the frame; a lens having an upper side and a lower side and left and right sides, on each of which a respective second stop hole is provided at a position corresponding to each respective first stop hole in the frame; and a pair of left and right belt arms each having bifurcated portions and a branch portion, on each end of the bifurcated and branch portions is provided with a lock mechanism. The frame and the lens are placed on each other and the respective first and second stop holes are aligned. The respective first and second stop holes can be brought into either a lock state by the lock mechanisms of the belt arms to secure the frame, the lens, and the pair of left and right belt arms, or an unlock state by the lock mechanisms where the lock state is released to separate them.

In the goggles of the present invention, when the respective first and second stop holes are brought into the lock state by the lock mechanism of the belt arm, a gap may be provided between the bifurcated portions of the belt arms and a surface of the lens.

Further, in the goggles of the present invention, the frame may have a nose pad portion which is recessed in a middle portion of the lower frame and inside of which a groove is provided. The lens may have a fitting portion which is recessed in a middle portion of the lower side fitted into the groove in the lower frame.

In the goggles of the present invention, the lock mechanism includes a lock pin, a sleeve, a knob and a stopper. The knob is provided on a step on the end of each bifurcated portion of the belt arms and rotated either downward to a side position from an upper position or upward from the side position to the upper position. Upward rotation of the knob provides a unlock state and downward rotation provides a lock state.

Further, in the goggles of the present invention, the frame is made of flexible soft elastic synthetic resin, and provided with a long groove having a U-shaped section in a peripheral wall adjacent to a surface of the frame in contact with the lens.

Since the goggles of the present invention is constituted as stated above, the lens of the goggles can be readily replaced with a lens having optimum visibility performance according to changes in natural environment due to the intensity of the sun, snowfall or rainfall.

Further, in the goggles of the present invention, the lens can be prevented from being touched by a wearer's hands in replacement, and thus even if a wearer has gloves on, the gloves are unlikely to touch the lens and the lens can be prevented from being rubbed and scratched.

In the goggles of the present invention, the lock mechanism is prevented from malfunctions, thereby reducing the possibility of unwanted removal of the lens from the frame.

Further, the goggles of the present invention are, of course, also suitable for use for sports that do not require a helmet. Thus the goggles are suitable for sports both requiring a helmet and not requiring it and the versatility is enhanced.

The goggles of the present invention have high shock absorbing properties, thereby preventing the frame and/or the lens from breaking, and a wearer from being injured.

DETAILED DESCRIPTION OF THE PREFERRED EMBODIMENTS

Embodiments of goggles of the present invention will be described below in detail with reference to the drawings.

The goggles of the present invention include a frame 1, a lens 2, a pair of belt arms 3 and a pair of fitting belts 4, as main structural members.

Figure 1:
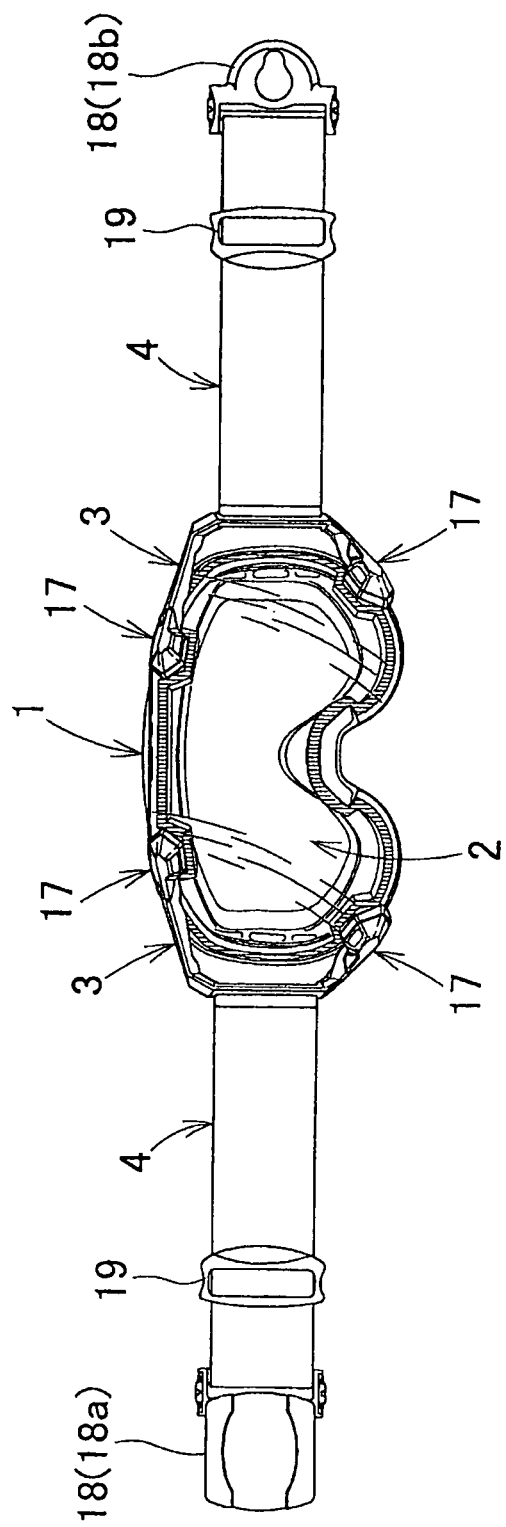
FIG. 1 is a front view of goggles according to the present invention.
Figure 2A:
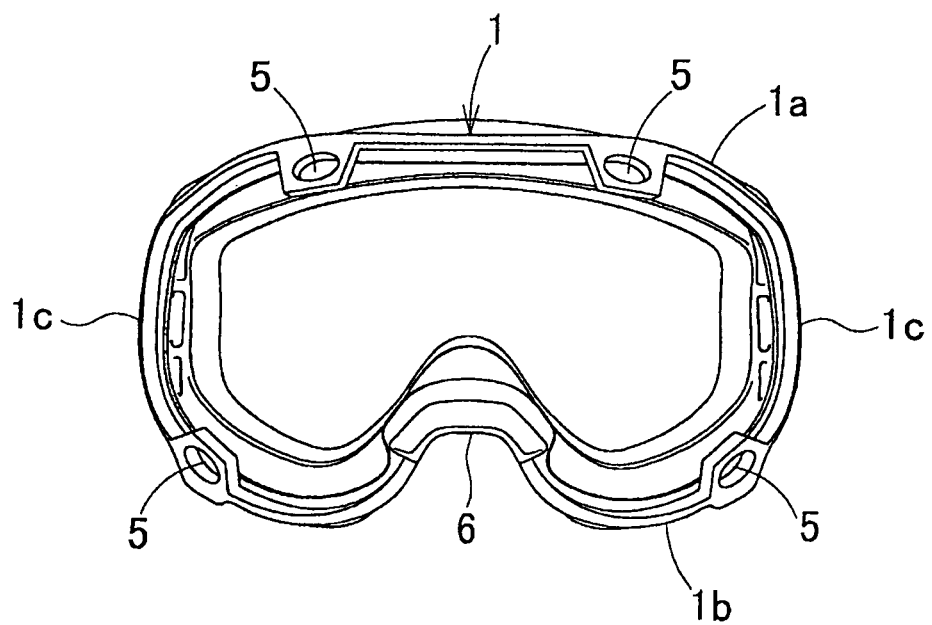
FIG. 2A is a front view of a frame of the goggles according to the present invention.

The frame 1 is generally made of flexible soft elastic synthetic resin or the like. The frame 1 has stop holes 5 (first stop holes) in four positions: left and right positions of upper and lower frame members in a periphery of a surface of the frame in contact with the lens 2. More specifically, as shown in FIG. 2A, one stop hole 5 is provided each left and right of a middle of both of a horizontally elongated upper frame member 1a and a horizontally elongated lower frame member 1b of the frame 1. Further, the lower side of the frame (i.e. the lower frame member 1b) has a nose pad portion 6 formed by recessing the middle portion. A groove 7a is provided inside the nose pad portion 6, and a pawl 8a is provided in the groove 7a (see FIG. 5A). The frame 1, as shown in FIG. 2A, is a surrounding frame including left and right frame members 1c, the upper frame member 1a and the lower frame member 1b, but may include only the upper frame member 1a and the lower frame member 1b.

Figure 5A:
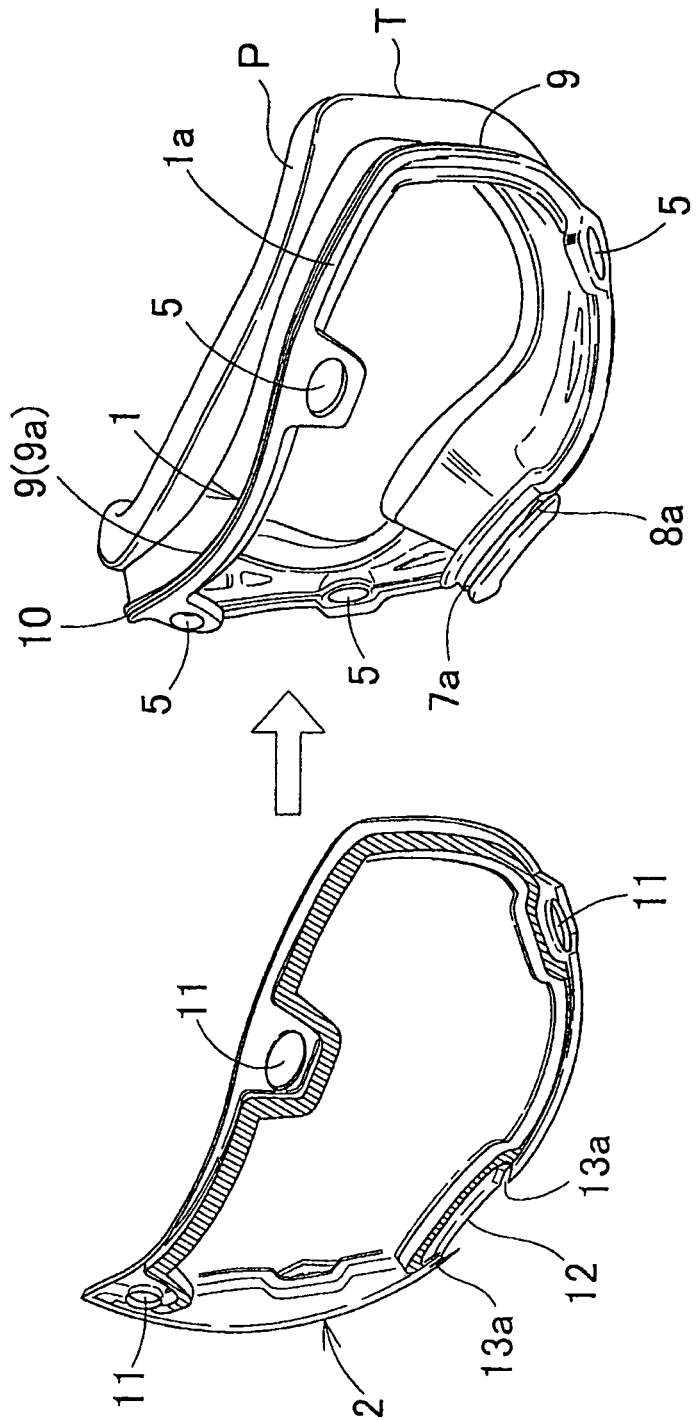
FIG. 5A is a perspective view showing a state before the lens is placed on the frame of the goggles according to the present invention.
Figure 6A:
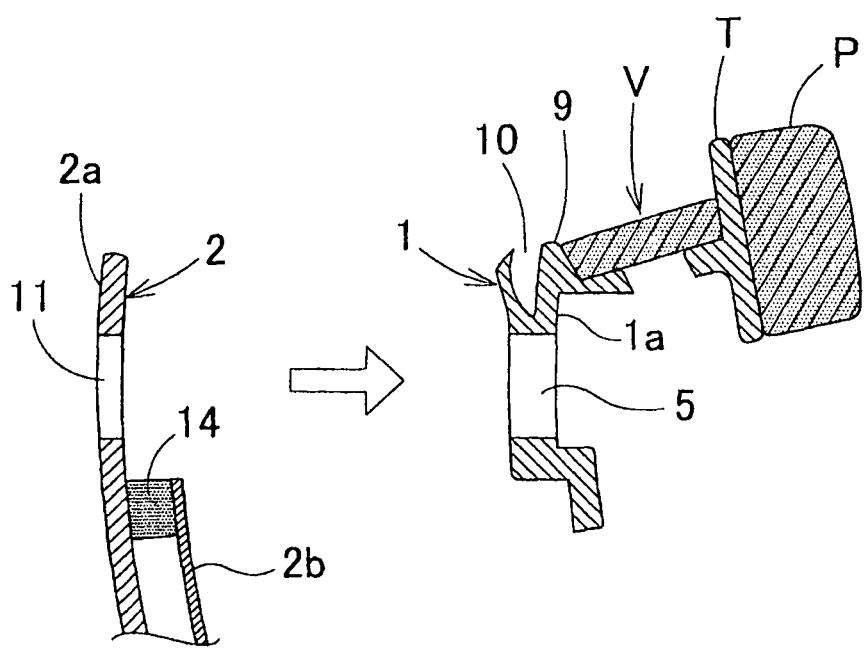
FIG. 6A is a partial sectional view showing the state before the lens is placed on the frame of the goggles according to the present invention.

Further, a long groove 10 having a U-shaped section is provided in a peripheral wall 9 adjacent to a surface of the frame 1 which is in contact with the lens 2 (see FIG. 6A). The long groove 10 is preferably provided across the entire peripheral wall 9 and serves as a cushion for absorbing an impact applied to the lens 2 from front when a wearer falls down, thereby preventing the lens 2 from breaking and preventing the wearer from being injured. The long groove 10 also serves as a trough through which, when the goggles are used in the rain, rainwater flows out without staying in the peripheral wall 9. If the function only as a trough is required, it is sufficient that the long groove 10 is provided across at least the entire upper wall 9a of the peripheral wall 9 (see FIG. 5A).

The frame 1 has a patch T on a rear side, and the patch T has a sponge pad P that is to abut on a wearer's face. Between the frame 1 and the patch T, a ventilation portion V may be provided if required.

The lens 2 is a single lens, and preferably made of a material such as an acrylic resin plate that has high scratch resistance and can filter out ultraviolet rays. Stop holes 11 (second stop holes) are provided in four positions: left and right positions of upper and lower sides in a periphery of a surface which contacts with frame 1. More specifically, respective stop holes 11 are provided on upper and lower sides of the lens 2 in positions corresponding to the respective stop holes 5 on both of the upper frame 1a and the lower frame 1b. A lower side of the lens has a fitting portion 12 recessed inward in a middle portion, and a notch 13a is provided in the fitting portion 12.

Figure 2B:
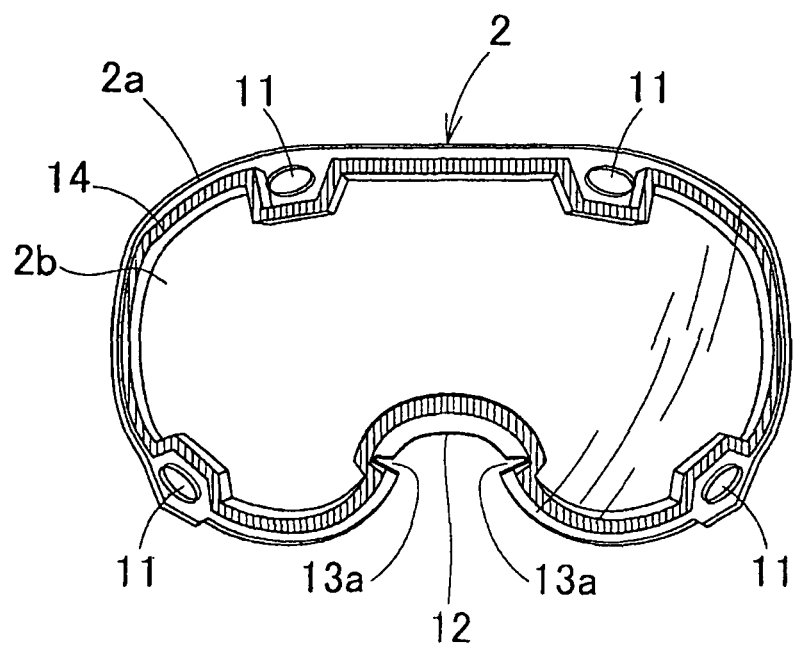
FIG. 2B is a front view of a lens of the goggles according to the present invention.
Figure 2C:
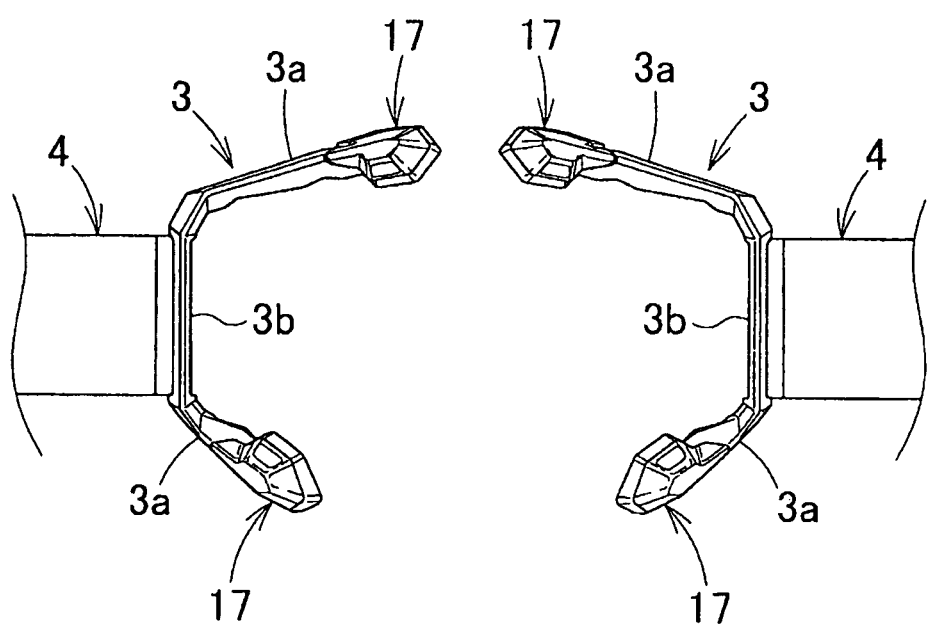
FIG. 2C is a front view of belt arms of the goggles according to the present invention.

Further, the lens 2 may be a double-lens including an outer lens 2a and an inner lens 2b attached to each other by a double sided adhesive tape 14. In this case, the outer lens 2a may be formed to extend beyond the circumference of the inner lens 2b, and the stop holes 11 may be provided in upper and lower sides of the outer lens 2a which extend beyond the inner lens 2b, as shown in FIG. 2B.

The pair of left and right belt arms 3, made of elastic synthetic resin with high bending strength, are respectively formed as a substantially squared U-shaped frame body having bifurcated portions 3a and 3a. Each of the end of the bifurcated portions 3a and 3a has a step (a step-down portion) 15, in the middle of which a through hole 16 is provided. A lock mechanism 17 is provided at each end of the bifurcated portions 3a and 3a. Further, the pair of fitting belts 4 are respectively coupled to outer ends 3b of the respective frame bodies.

The pair of left and right fitting belts 4 are formed of stretching elastic belts. One ends of the pair of fitting belts 4 are respectively coupled to the outer ends 3b of the frame bodies of the pair of belt arms 3. The other end of each of the pair of fitting belts 4 has a male body or a female body 18a or 18b of a buckle 18 so that the pair of fitting belts 4 can be coupled or uncoupled by the male and female bodies 18a and 18b. Further, each of the pair of fitting belts 4 has a length adjustment member 19.

In the goggles of the present invention, the frame 1 and the lens 2 are placed on each other and the respective corresponding stop holes 5 and 11 are aligned. The step holes 5 and 11 can be brought into a lock state by the lock mechanism 17 of each of the belt arms 3 so as to secure the frame 1, the lens 2, and the pair of left and right belt arms 3. And the lock state can be released to separate the frame 1, the lens 2, and the pair of left and right belt arms 3.

In the goggles of the present invention, when the stop holes 5 and 11 are brought into the lock state by the lock mechanism 17 of the belt arm 3, a gap S is formed between the bifurcated portions 3a and 3a of the belt arms and the surface of the lens 2. With such a gap S, the belt arm 3 is spaced apart outward from the surface of the lens 2. Thus, in use for sports that require a helmet, the fitting belt 4 coupled to the belt arm 3 is not pushed outward by a thickness of the helmet, the frame 1 does not rise apart from the wearer's face and maintains a tight contact therewith.

As shown in FIGS. 3A, 3B, 4A and 4B, each of the lock mechanisms 17 includes a lock pin 20, a sleeve 21, a knob 22, and a stopper 23.

The lock pin 20 has a lock body 20b at one end of a shaft body 20a, and is in a generally substantially T shape in the plan view. Recesses 24 and 24 are formed oppositely at a tip end of the shaft body 20a of the lock pin 20. In case the stop hole 5 provided in the frame 1 has an elliptical shape, the lock body 20b of the lock pin 20 is formed into an elliptical shape so as to fit in the stop hole 5. Thus, when the knob 22 described later is rotated upward into an unlock state, the lock body 20b does not lock the stop hole 5 provided in the frame 1, and when the knob 22 is rotated downward into a lock state, the lock body 20b locks the stop hole 5. The shape of the lock body 20b is not limited to the elliptical shape as long as the lock body 20b has a shape with which the lock body 20b can either lock or unlock the stop hole 5 by rotation of the knob 22.

The sleeve 21 fits in the stop hole 5 provided in the frame 1 and the stop hole 11 provided in the lens 2. In case the stop holes 5 and 11 have a circular section, the sleeve 21 is formed to have a cylindrical shape so as to fit into the stop holes 5 and 11, and in case the stop holes 5 and 11 have an elliptical section, the sleeve 21 is formed to have a elliptical cylindrical shape so as to fit into the stop holes 5 and 11. The sleeve is shaped according to the shape of the stop holes 5 and 11, and has a through hole 21a for receiving the shaft body 20a of the lock pin 20.

Figure 3A:
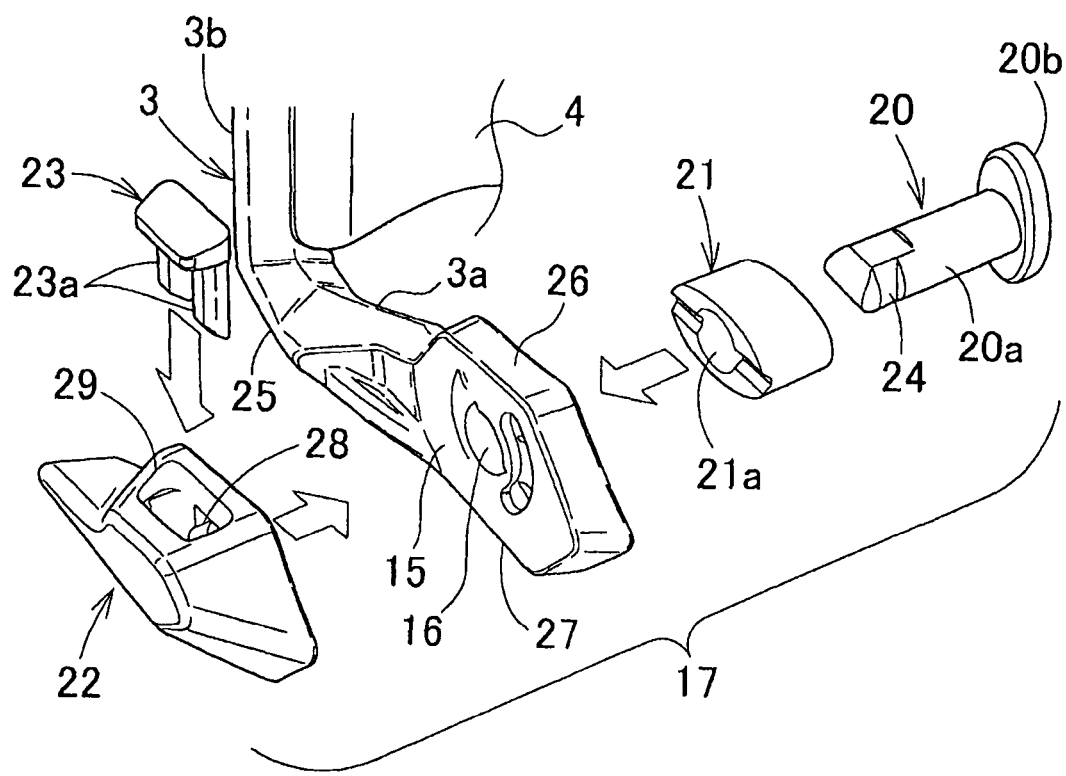
FIG. 3A is an exploded perspective view showing a lock state of a lock mechanism at an end of one of the belt arms of the goggles according to the present invention.
Figure 3B:
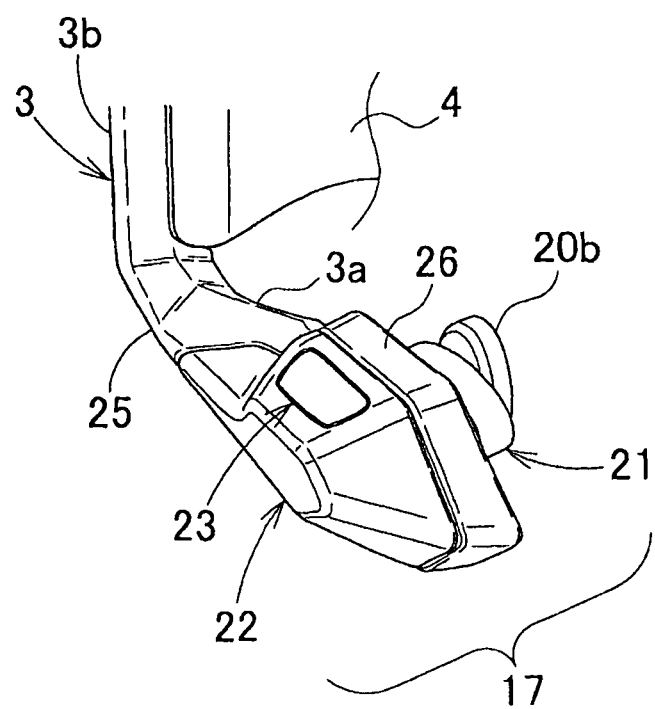
FIG. 3B is an assembled perspective view showing the lock state of the lock mechanism at the end of the one of the belt arms of the goggles according to the present invention.
Figure 4A:
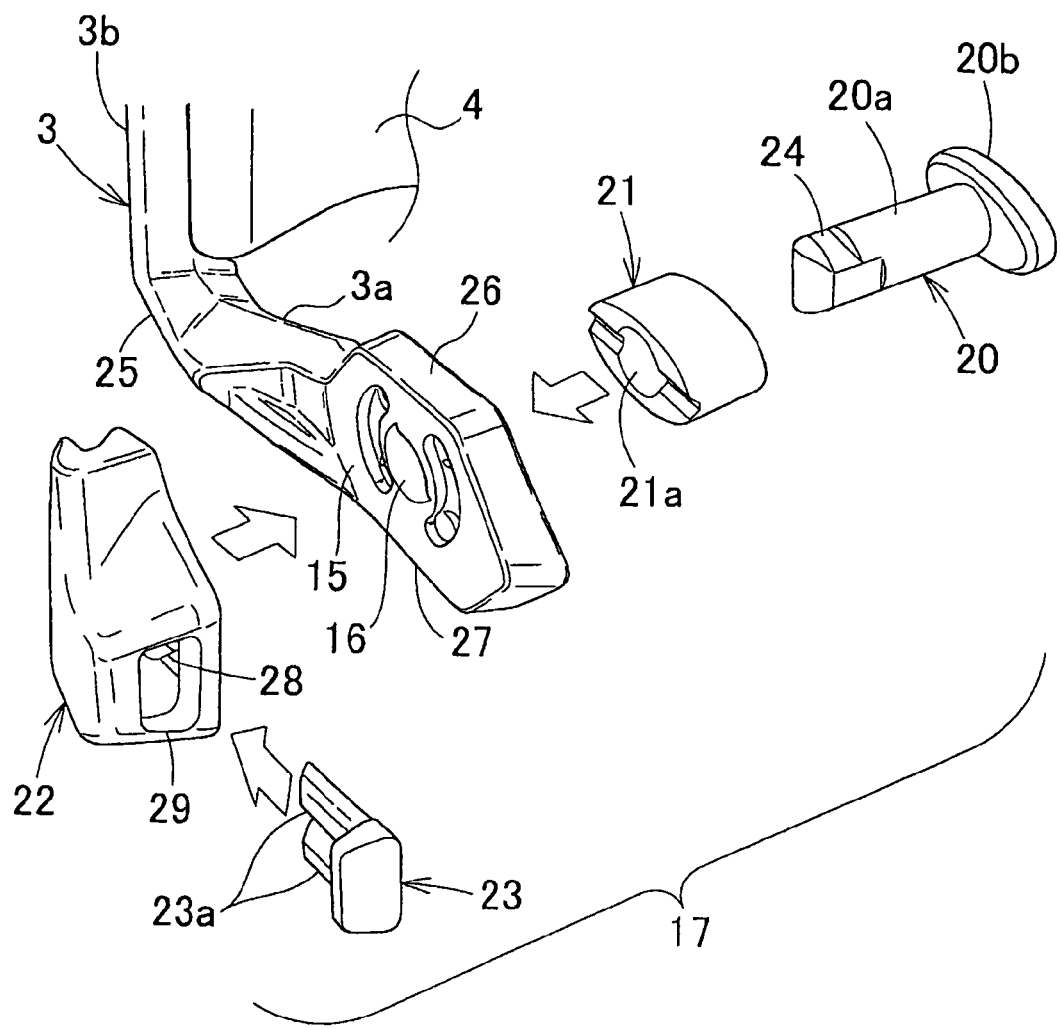
FIG. 4A is an exploded perspective view showing an unlock state of the lock mechanism at the end of the one of the belt arms of the goggles according to the present invention.
Figure 4B:
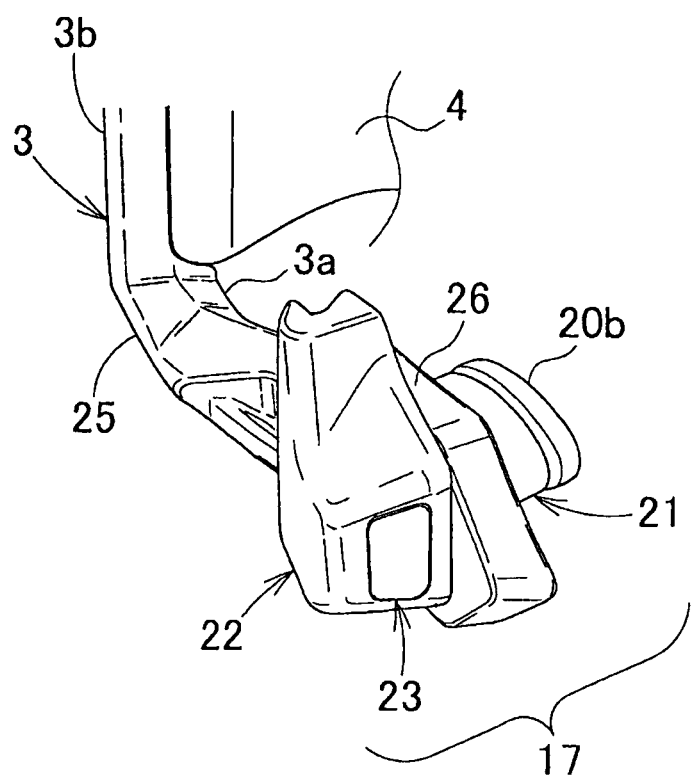
FIG. 4B is an assembled perspective view showing the unlock state of the lock mechanism at the end of the one of the belt arms of the goggles according to the present invention.

The knob 22 is provided on the step 15 at the end of the bifurcated portion 3a of the belt arm 3 so as to be rotatable down to a side position from an upper position into a lock state or up to the upper position from the side position into an unlock state. In the lock state, an outer edge 25, the upper side surface 26 and the lower side surface 27 of the bifurcated portion 3a of the belt arm 3 are respectively flush with the corresponding edge and surfaces of the knob 22, as shown in FIG. 3B. The knob 22 has an insertion hole 28 which receives the tip end of the shaft body 20a of the lock pin 20, and another insertion hole 29 which receives a stopper 23 and is perpendicularly to and communicating with the insertion hole 28.

The stopper 23 has pawls 23a. When the stopper 23 is inserted into the insertion hole 29 in the knob 22, the pawls 23 hold, from opposite sides, the recesses 24 and 24 formed in the tip end of the shaft body 20a of the lock pin 20 which has been inserted into the insertion hole 28 in the knob 22 so that the stopper 23 secures the tip end of the shaft body 20a. The structure and/or shape of the stopper 23 is not limited to the above, as long as it is insertable into the insertion hole 29 in the knob 22 to secure the tip end of the shaft body 20a of the lock pin 20.

The end of the bifurcated portion 3a of the belt arm 3 has a through hole 16. For the purpose of incidence of the holes, with the through hole 16, the through hole 21a in the sleeve 21 fitted in the stop holes 5 and 11 in the frame 1 and the lens 2 is aligned from inside of the belt arm 3, and the insertion hole 28 in the knob 22 positioned on the step 15 at the end of the bifurcated portion 3a of the belt arm 3 is aligned from outside of the belt arm 3. Subsequently, the shaft body 20a of the lock pin 20 is passed through the through hole 21a in the sleeve 21 and the through hole 16 in the end of the bifurcated portion 3a of the belt arm 3, and the tip end of the shaft body 20a is inserted into the insertion hole 28 in the knob 22. Then, the stopper 23 is inserted into the insertion hole 29 perpendicular to and communicating with the insertion hole 28 in the knob 22, the recesses 24 and 24 in the tip end of the shaft body 20a of the lock pin 20 is held by the pawls 23a of the stopper 23 from opposite sides so that the tip end of the shaft body 20a is secured to the knob 22. As stated above, the lock mechanism 17 is provided at the end of the bifurcated portion 3a of the belt arm 3.

Figure 5B:
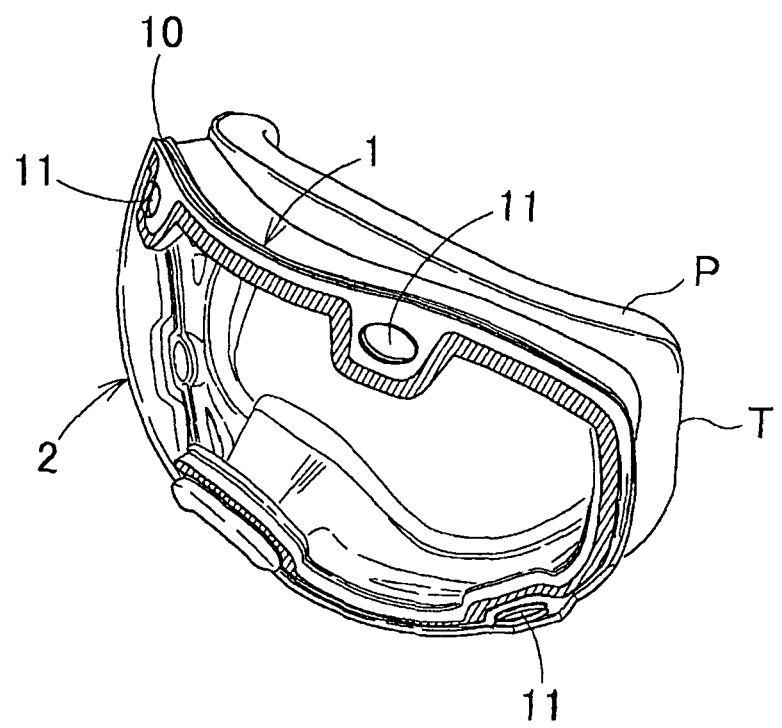
FIG. 5B is a perspective view showing a state after the lens is mounted on the frame of the goggles according to the present invention.

The main structural members of the goggles of the present invention are configured as described above. As shown in FIGS. 5A and 5B, the fitting portion 12 of the lens 2 is fitted into the groove 7a of the frame 1. More specifically, the fitting portion 12 of the lens 2 is fitted into the groove 7a of the frame 1 so that the pawl 8a in the groove 7a in the frame 1 fits in the notch 13a in the fitting portion 12 of the lens 2. Thus, the stop hole 5 in the frame 1 and the stop hole 11 in the lens 2 are aligned with each other, as shown in FIG. 5B.

As shown in FIGS. 5C to 5E and 6B to 6D, in the goggles of the present invention, the respective bifurcated portions 3a and 3a of the belt arms 3 are secured to the aligned stop holes 5 and 11 by the lock mechanisms 17 provided at the ends of the bifurcated portions 3a and 3a of the belt arms 3. Then, the lens 2 is mounted to the frame 1.

Figure 5C:
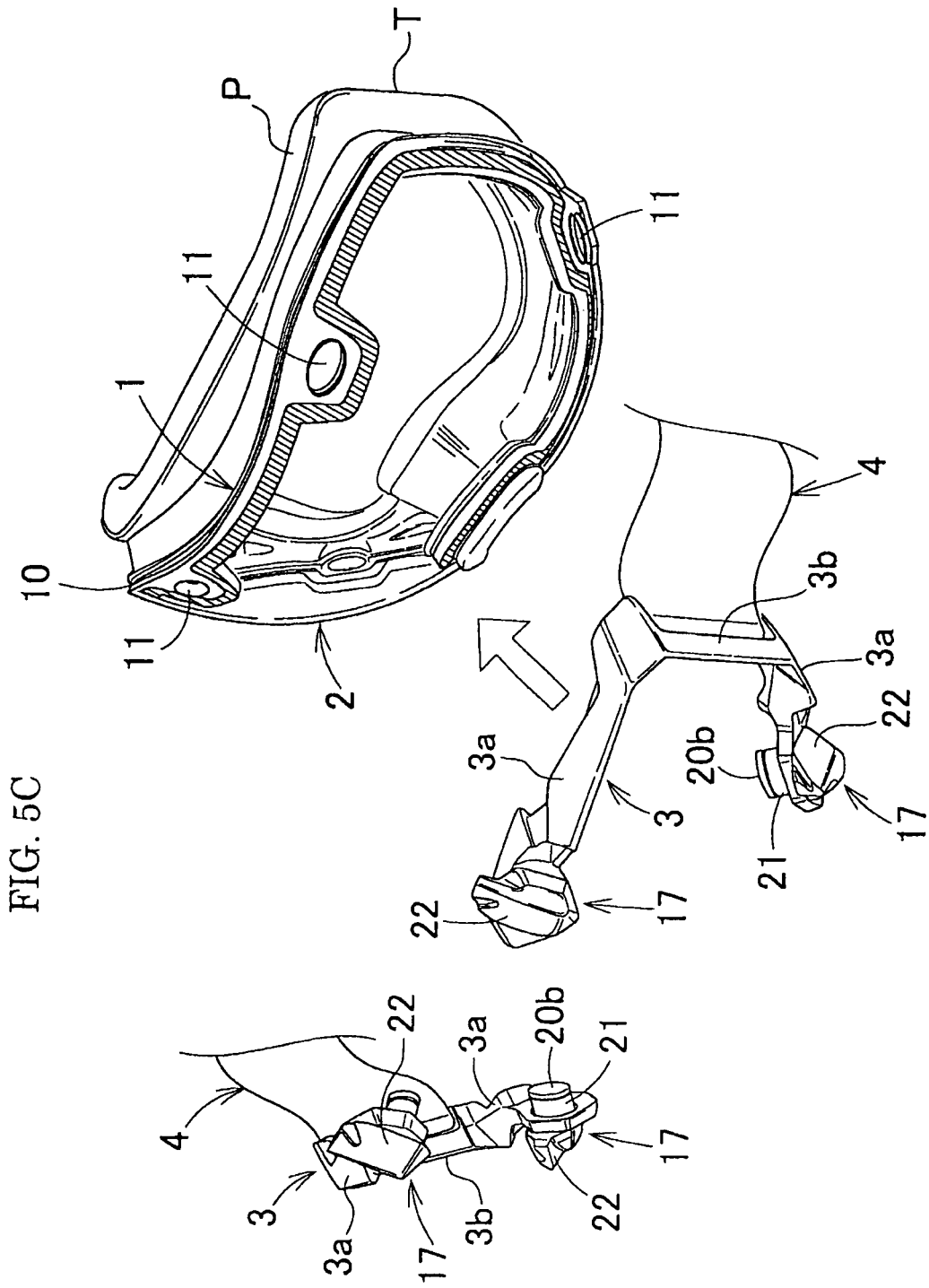
FIG. 5C is a perspective view showing a state before the belt arms are put on the lens in the state in FIG. 5B.
Figure 5D:
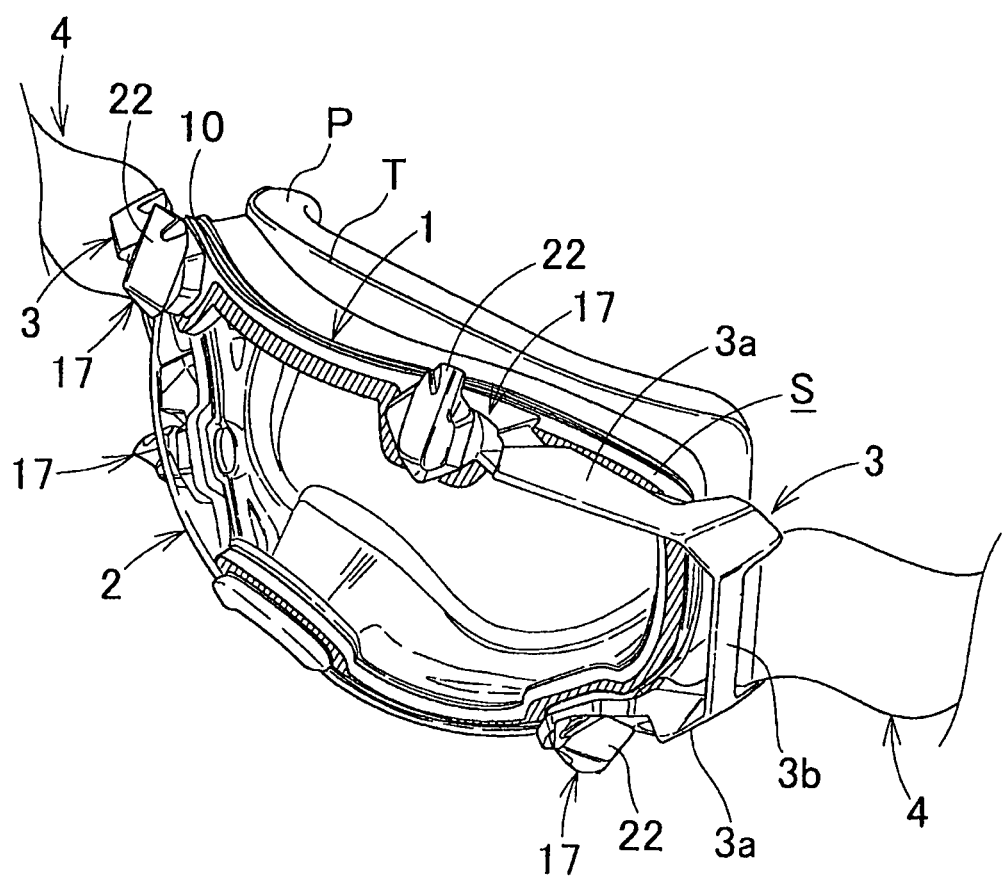
FIG. 5D is a perspective view showing a state after the belt arms are fixed on the lens in the state in FIG. 5B.
Figure 5E:
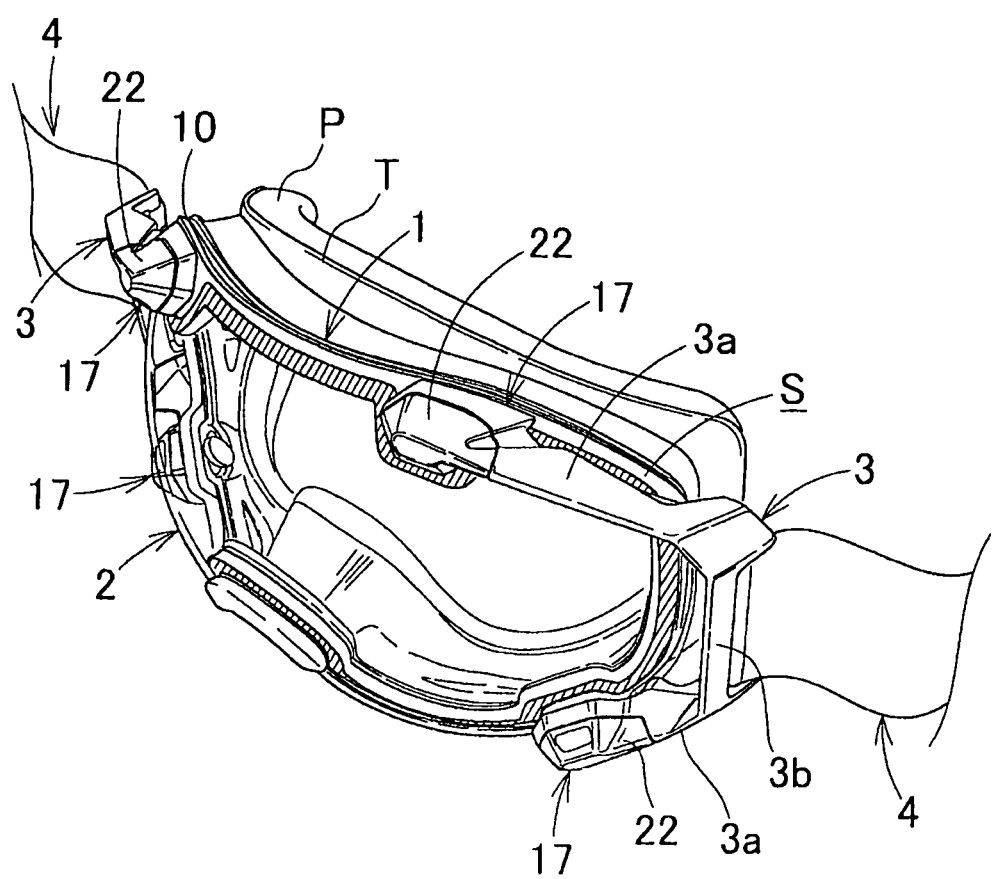
FIG. 5E is a perspective view of a fixed state where a knob of the lock mechanism at the end of each belt arm in the state in FIG. 5D has been manipulated to secure the frame, the lens and the belt arms.
Figure 6B:
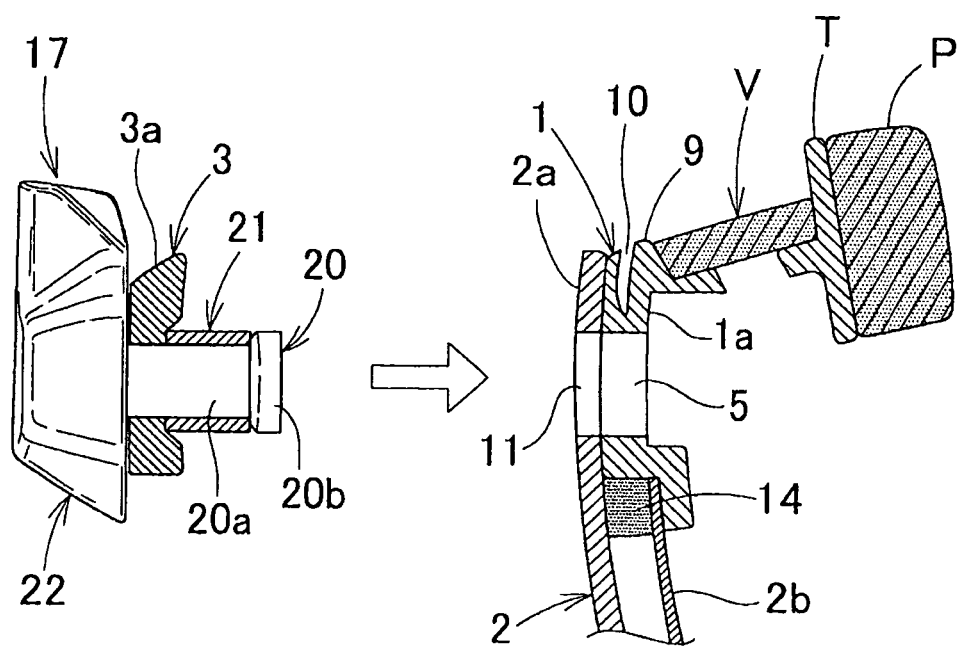
FIG. 6B is a partial sectional view showing a state before a lock pin of the lock mechanism at the end of each belt arm is passed through the stop holes in both the lens and the frame in which the lens is placed on the frame.
Figure 6C:
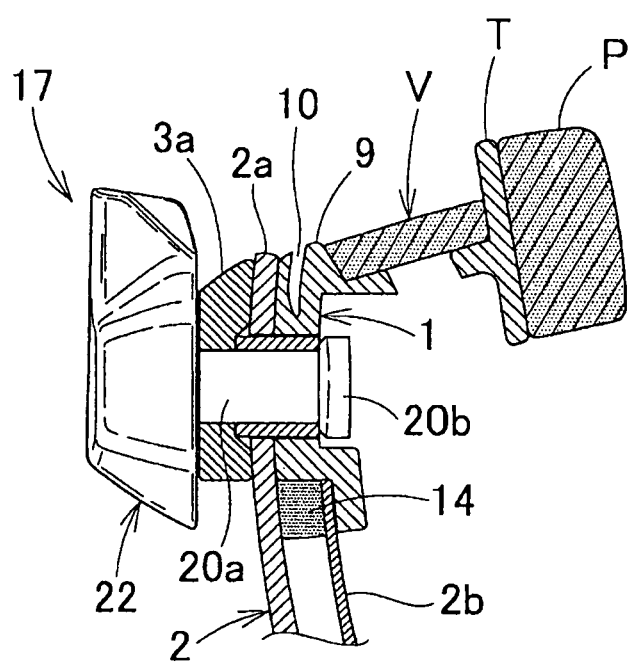
FIG. 6C is a partial sectional view showing a state after the lens is placed on the frame and the lock pin of the lock mechanism at the end of each belt arm is passed through the stop holes in both the lens and the frame of the goggles according to the present invention.
Figure 6D:
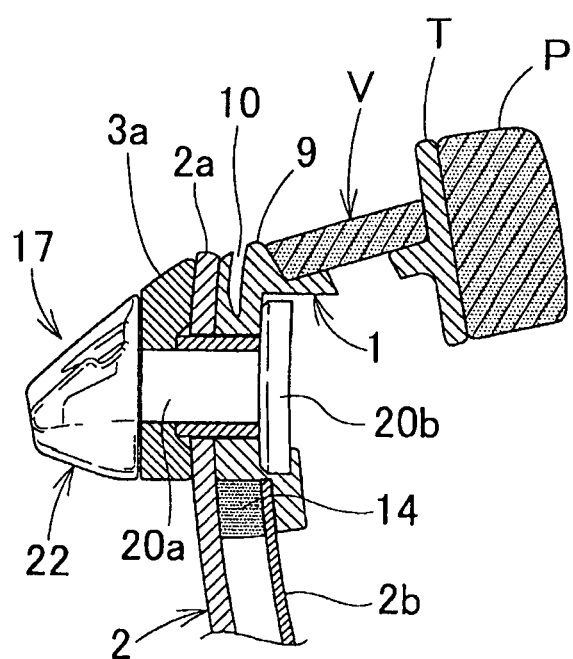
FIG. 6D is a partial sectional view of a state where the knob of the lock mechanism at the end of each belt arm shown in FIG. 6C has been manipulated to secure the frame, the lens and the belt arm.

Specifically, the lock body 20b of the lock pin 20 and the sleeve 21 of the lock mechanism 17 which has brought into the unlock state by rotating the knob 22 upward as shown in FIGS. 5C and 6B are inserted into the stop holes 5 and 11 as shown in FIGS. 5D and 6C. Then, as shown in FIGS. 5E and 6D, the knob 22 is rotated down to the side position from the upper position into the lock state, then the lock body 20b of the lock pin 20 locks in the stop hole 5 in the frame 1, and the bifurcated portion 3a of the belt arm 3 is secured to the stop holes 5 and 11, and thereby the lens 2 is mounted to the frame 1. Detachment of the lens 2 from the frame 1 may be done by the reverse procedure of the above.

Thus, in the goggles of the present invention, the lens 2 may be readily attached to or detached from the frame 1, and quickly replaced in replacement.

Further, in the goggles of the present invention, the knob 22 is not directly provided on the lens 2 but provided on the belt arm 3. Therefore, in change between the lock state and the unlock state by the rotation of the knob 22, wearer's hands are unlikely to touch the lens 2 and it prevents the surface of the lens 2 from being rubbed and scratched.

Further, in the goggles of the present invention, the rotation in a direction in which an external force is easily given to the goggles when a wearer's hand or other object touches the knob 22 (i.e. the rotation down to the side position from the upper position) leads to the lock state. On the other hand, the rotation in a direction in which an external force is unlikely given to the goggles (i.e. the rotation upward to the upper position from the side position) leads to the unlock state. Consequently, the possibility of unintended removal of the lens 2 from the frame 1 by malfunction of the lock mechanism 17 is reduced.

Further, in the goggles of the present invention, while the knob 22 is in the lock state, the outer edge 25 and the upper and lower side surfaces 26 and 27 of the bifurcated portion 3a of the belt arm 3 are flush with the corresponding edge and surfaces of the knob 22, and thus the knob 22 does not protrude out from the belt arm 3. An external force is then not easily applied to the knob 22 and the lock mechanism is prevented from malfunctions. Thereby the possibility of inadvertent removal of the lens 2 from the frame 1 is reduced.

Figure 7:
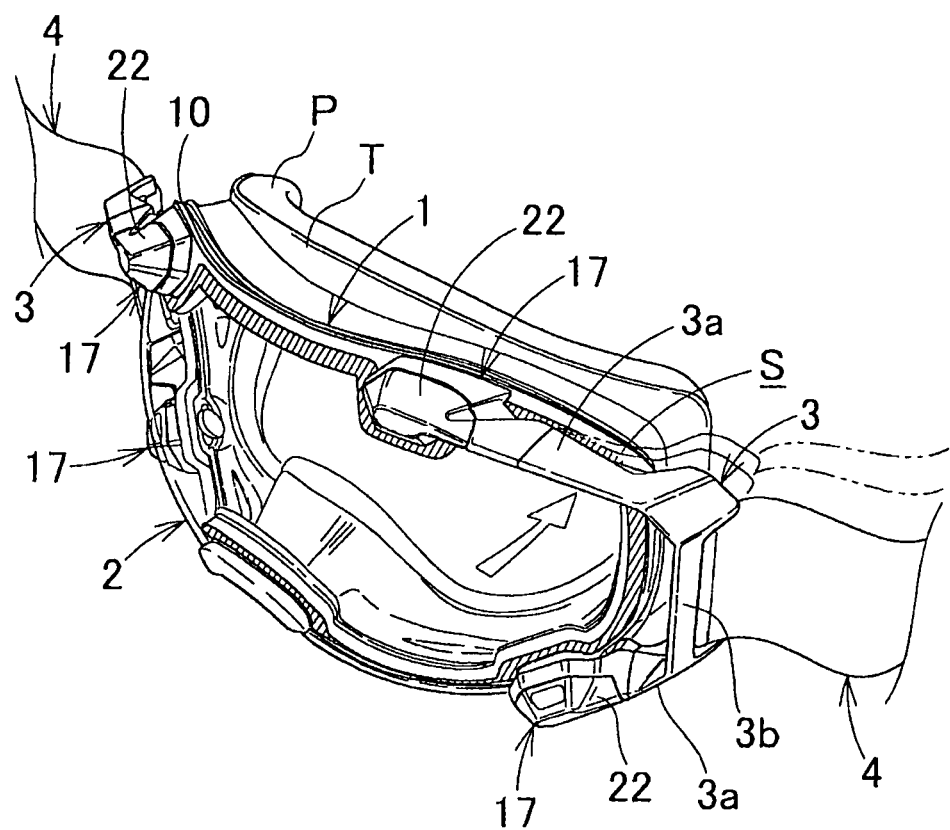
FIG. 7 is a perspective view showing another embodiment of belt arms of the goggles according to the present invention.
Figure 8:
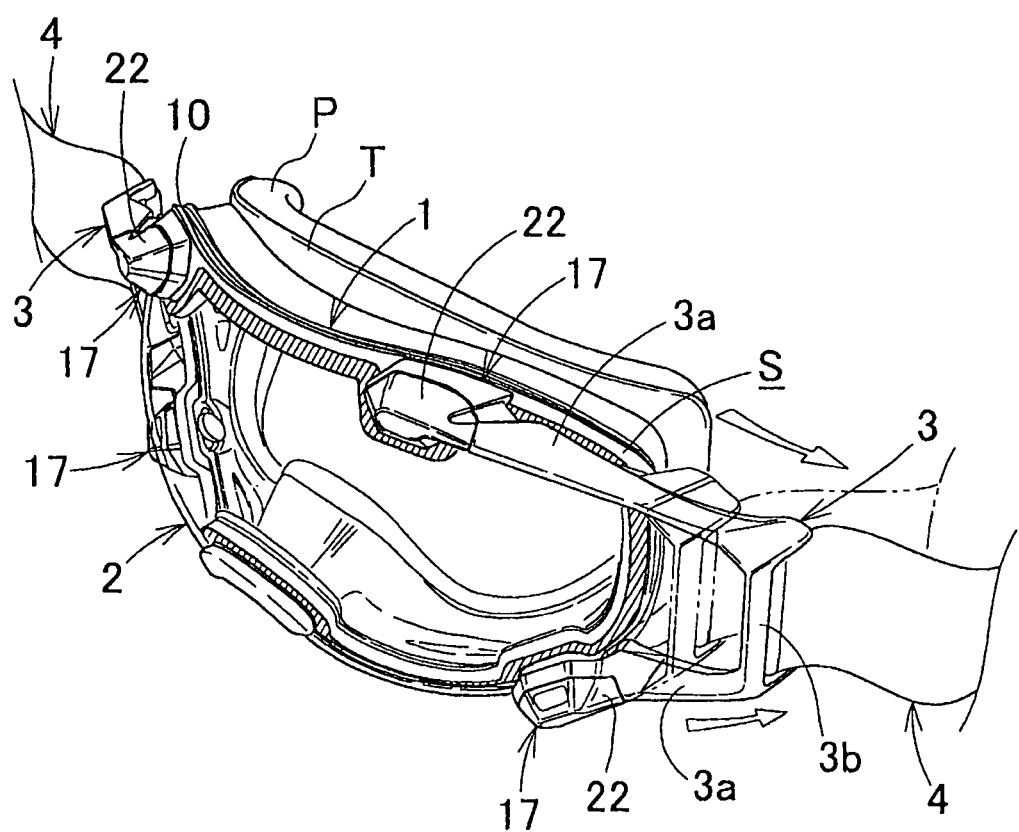
FIG. 8 is a perspective view showing another embodiment of belt arms of the goggles according to the present invention.

In the goggles of the present invention, the gap S is provided between the surface of the lens 2 and the bifurcated portion 3a of the belt arm 3 as shown in FIG. 7, or in addition to the gap S, the bifurcated portion 3a of the belt arm 3 is made of soft elastic synthetic resin, or increased in length as shown in FIG. 8. And, even when the goggles are used for doing sports that require a helmet, the fitting belt 4 is not pushed outward by a thickness of the helmet, the frame 1 does not rise apart from the wearer's face and lose a tight contact with the wearer's face.

Figure 9:
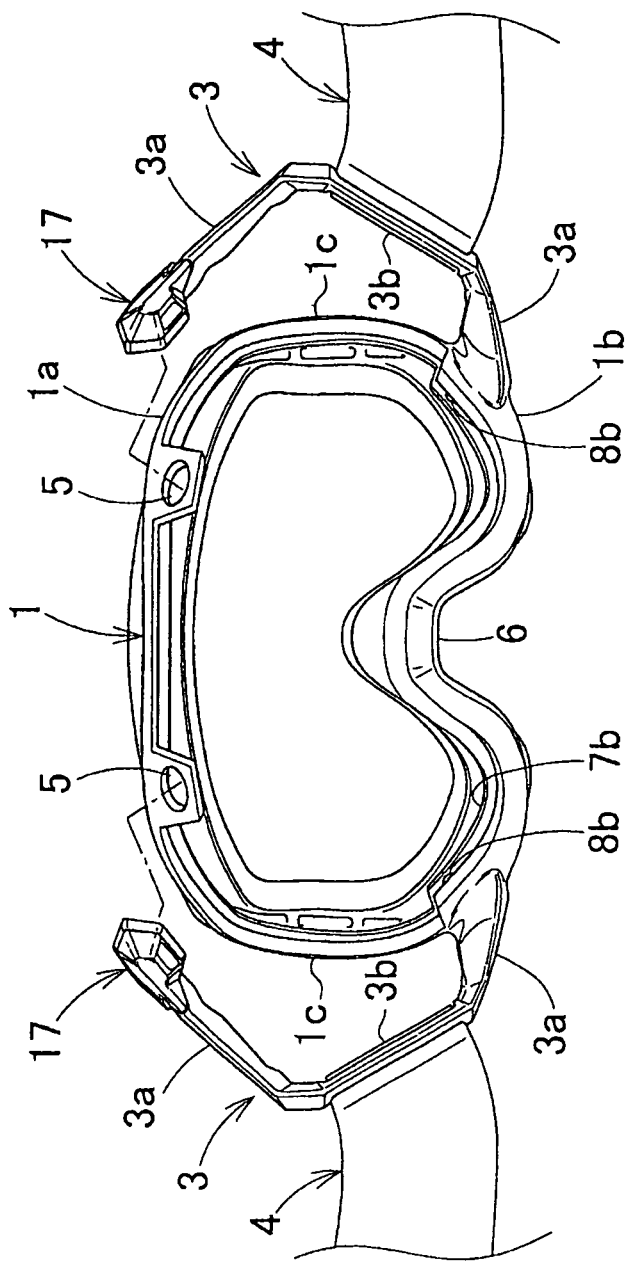
FIG. 9 is a front view showing another embodiment of a frame and belt arms of the goggles according to the present invention.
Figure 10:
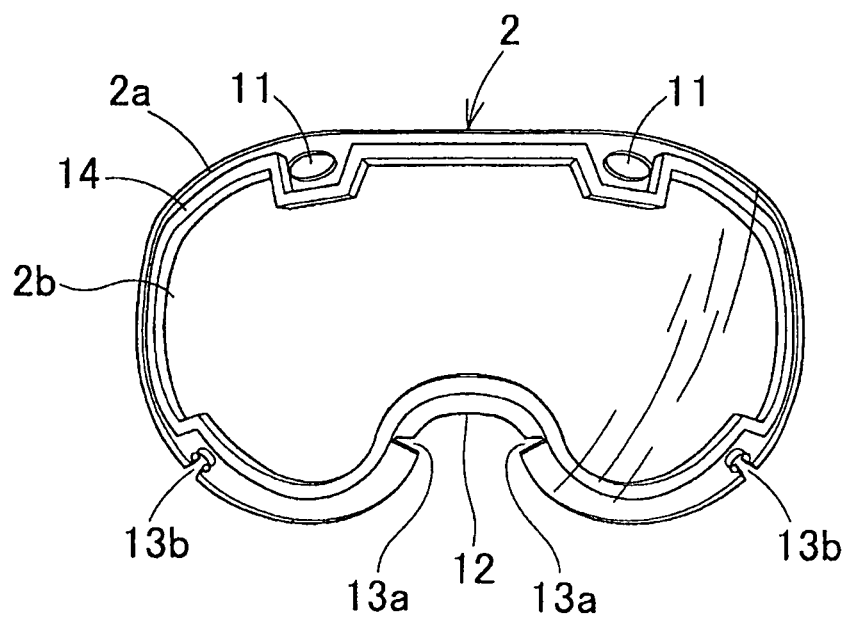
FIG. 10 is a front view showing another embodiment of a lens of the goggles according to the present invention.

Further, another embodiment of goggles of the present invention is shown in FIGS. 9 and 10.

As shown in FIG. 9, the goggles of the present invention include one stop hole 5 in each of left and right sides of the middle of the upper frame member 1a of the frame 1. On the upper side of the lens 2, one stop hole 11 is provided at a position corresponding to each of the stop holes 5 in the frame 1. The lock mechanism 17 is provided at an end of one of the bifurcated portions 3a and 3a, that is, the end of an upper bifurcated portion 3a of each of the pair of left and right belt arms 3.

Then, the frame 1 and the lens 2 are place on each other, and the respective stop holes 5 and 11 are aligned. The stop holes 5 and 11 are brought into the lock state by the lock mechanism 17 of the belt arm 3 to secure the frame 1, the lens 2, and the one end of the bifurcated portions 3a and 3a of each of the pair of left and right belt arms 3. The lock state can be released to allow them to separate.

Further, an end of the other of the bifurcated portions 3a and 3a of the belt arm 3, that is, the end of a lower bifurcated portion 3a of the belt arm 3, is coupled to the lower frame member 1b of the frame 1. In the drawings, the end of the lower bifurcated portion 3a of the belt arm 3 is fixed to the lower frame member 1b of the frame 1, but may be pivoted.

The lower frame member 1b has a groove 7b, into which a lower edge of the lens 2 is fitted. In each of left and right ends of the groove 7b, a pawl 8b may be provided. In this case, the lower side of the lens 2 is provided with a notch 13b corresponding to each of the pawls 8b so that the pawl 8b fits into the notch 13b when the lower edge of the lens 2 is fitted into the groove 7b in the lower frame member 1b.

Further, in the goggles of the present invention, although not shown, one stop hole 5 may be provided in each of left and right of the middle of the lower frame member 1b of the frame 1. On the lower side of the lens 2, a stop hole 11 may also be provided at a position corresponding to the stop hole 5 in the lower frame member 1b. The lock mechanism 17 may be provided at an end of the other of the bifurcated portions 3a and 3a, that is, on the end of the lower bifurcated portion 3a of each of the pair of left and right belt arms 3.

Then, the frame 1 and the lens 2 are placed on each other and the respective stop holes 5 and 11 are aligned. The stop holes 5 and 11 are brought into the lock state by the lock mechanism 17 of the belt arm 3 to secure the frame 1, the lens 2, and the other the bifurcated portions 3a and 3a of each of the pair of left and right belt arms 3. The lock state can be released to allow them to separate.

Further, the end of the one of the bifurcated portions 3a and 3a, that is, the end of the upper bifurcated portion 3a of the belt arm 3 may be secured to or pivoted on the upper frame member 1a of the frame 1, thereby providing the coupling of them.

The upper frame member 1a is provided with the groove 7b, into which an upper edge of the lens 2 may be fitted.

Also in this embodiment, the lock mechanism 17 has the same structure as that described above.

Figure 11:
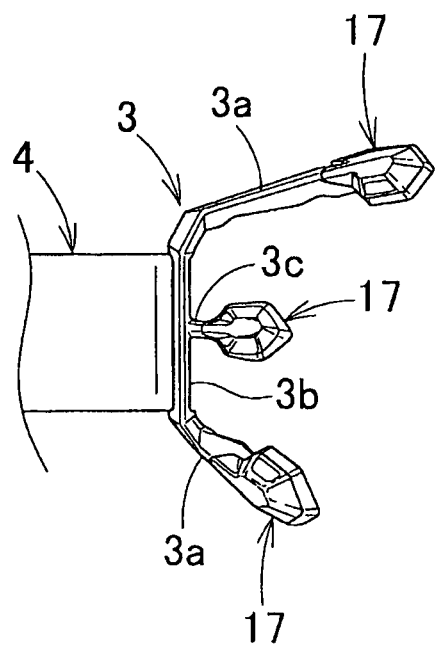
FIG. 11 is a front view showing a further embodiment of one of belt arms of the goggles according to the present invention.
Figure 12:
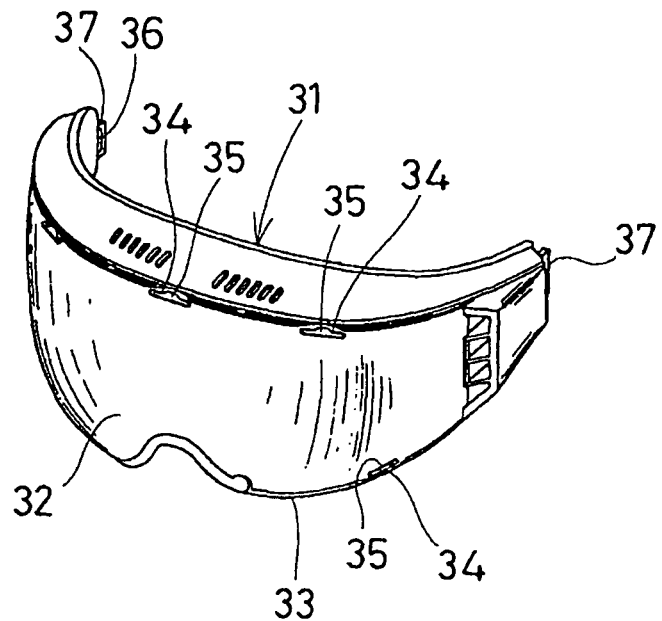
FIG. 12 is a perspective view showing an example of conventional goggles.
Figure 13:
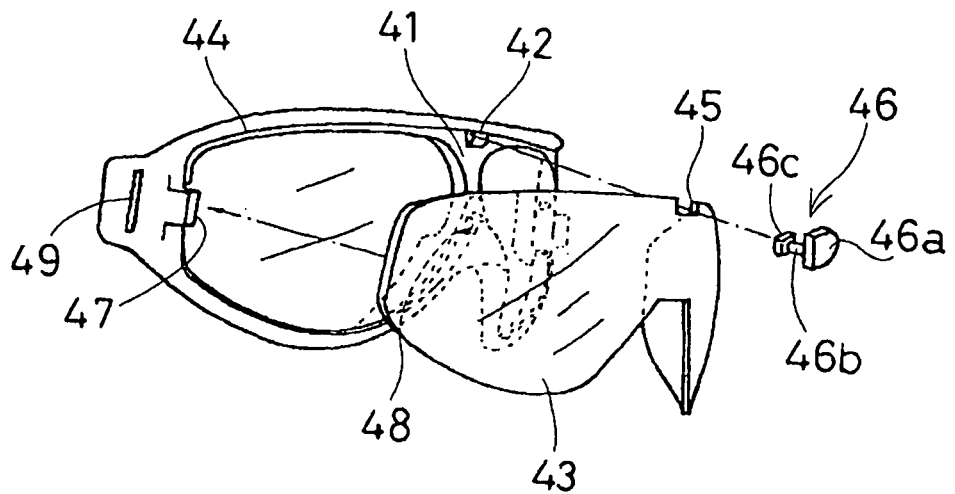
FIG. 13 is an exploded perspective view showing an example of a conventional lens mounting structure.
Figure 14:
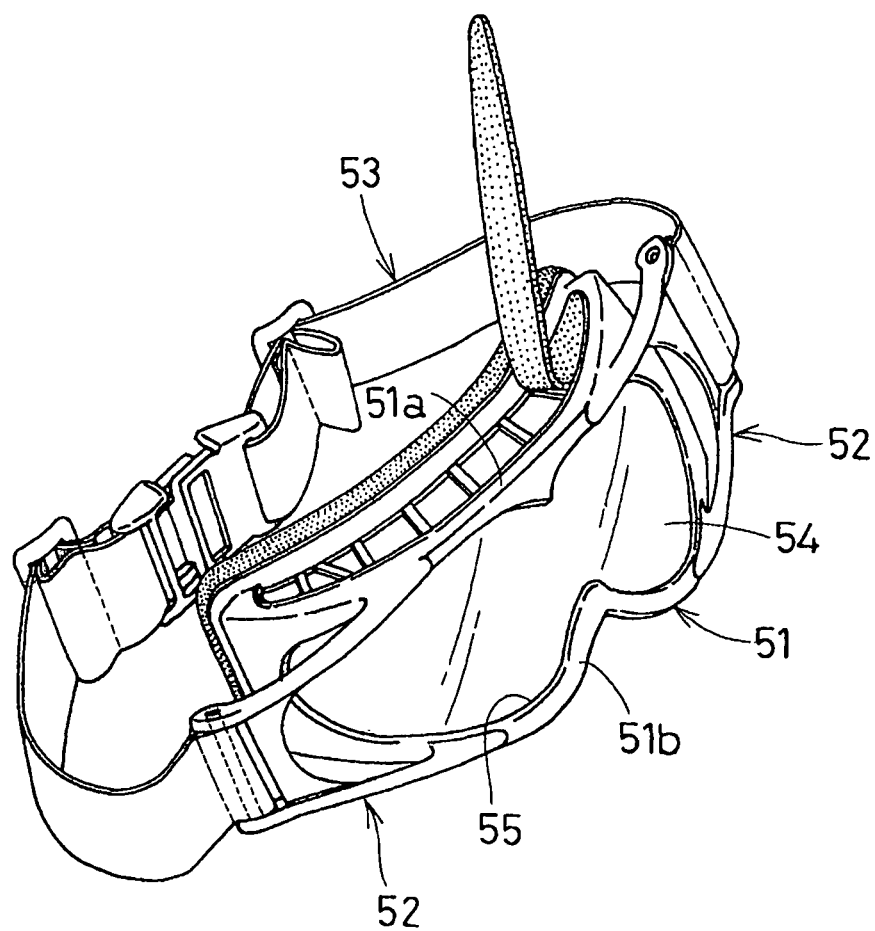
FIG. 14 is a perspective view showing another example of conventional goggles.

Further, in the goggles of the present invention, as shown in FIG. 11, each of the pair of left and right belt arms 3 and 3 may further have a branch portion 3c. The branch portion 3c protrudes from the outer end 3b as shown in FIG. 11, but may protrude from one of the bifurcated portions 3a and 3a.

In this case, although not shown, one stop hole 5 is provided in each of left and right of the middle of each of the upper frame member 1a and the lower frame member 1b and in each of left and right frame members 1c and 1c of the frame 1. The lens 2 has, on the upper, lower, left and right sides thereof respectively, a stop hole 11 in a position corresponding to each of the stop holes 5 in the frame 1. The lock mechanism 17 is provided at the end of each of the bifurcated portions 3a and 3a and the branch portion 3c of each of the pair of left and right belt arms 3.

Then, the frame 1 and the lens 2 are placed on each other, and the stop holes 5 and 11 are aligned. The stop holes 5 and 11 are brought into the lock state by the lock mechanism 17 of the belt arm 3 to secure the frame 1, the lens 2, the pair of left and right belt arms 3. The lock state can be released to allow them to separate.

Also, in the goggles of the present invention shown in FIG. 11, without providing the lock mechanism 17 at the end of the branch portion 3c, the end of the branch portion 3c may be coupled to the frame 1 by being secured to or pivoted on each of the left and right frame members 1c and 1c of the frame 1. In this case, each of the left and right sides of the lens 2 requires no stop hole 11.

Also in the goggles, the frame 1 and the lens 2 are placed on each other, and the respective stop holes 5 and 11 are aligned. The stop holes 5 and 11 are brought into the lock state by the lock mechanism 17 of the belt arm 3 to secure the frame 1, the lens 2, the bifurcated portions 3a and 3a of the pair of left and right belt arms 3. The lock state can be released to allow them to separate.

Also in this embodiment, the lock mechanism 17 has the same structure as described above.

What is claimed is:

1. Goggles comprising:
a frame on which a plurality of separate frame stop holes is provided, the frame including a horizontally elongated upper frame member and a horizontally elongated lower frame member, first, second, third and fourth separate frame stop holes of said plurality being located left of a middle of, and on, the upper frame member, right of the middle of, and on, the upper frame member, left of a middle of, and on, the lower frame member, and right of the middle of, and on, the lower frame member, respectively, with the first and second separate frame stop holes being located along a top of the frame and the third and fourth separate frame stop holes being located along a bottom of the frame;
a lens having an upper side and a lower side on each of which, in a periphery of a lens surface which contacts the frame, a respective lens stop hole of a plurality of lens stop holes is provided at a position corresponding to each of the first, second, third, and the fourth frame stop holes in the frame; and
a left belt arm adjacent a left side of the frame, and a right belt arm adjacent a right side of the frame, each belt arm being bifurcated into bifurcated portions, an end of each bifurcated portion being provided with a respective lock mechanism;

wherein the frame and the lens are placed on each other and respective frame and lens stop holes are aligned, the aligned respective frame and lens stop holes are, by the respective lock mechanism, brought into either a lock state to secure the frame, the lens and the left and right belt arms, or an unlock state where the lock state is released to separate the frame, the lens, and the left and right belt arms.

2. The goggles according to claim 1, wherein the lock state of the respective frame and lens stop holes by the respective lock mechanism provides a gap between the bifurcated portions of the belt arms and a front surface of the lens.

3. The goggles according to claim 1, wherein the frame has a nose pad portion which is recessed in a middle portion of the lower frame and provided with a groove inside thereof, and the lens has a fitting portion which is recessed in a middle portion of the lower side which is fitted into the groove in the lower frame.

4. The goggles according to claim 1, wherein the end of each bifurcated portion of each belt arm has a through hole, each lock mechanism includes a lock pin, a sleeve, a knob and a stopper, the lock pin extends through the sleeve, the aligned respective frame and lens stop holes and the through hole into the knob and is retained in the knob by the stopper, the knob is provided on a step on the end of the bifurcated portion of the belt arm, and rotated either downward from an upper position to a side position which provides the lock state or upward from the side position to the upper position which provides the unlock state.

5. The goggles according to claim 1, wherein the frame is made of flexible soft elastic synthetic resin, and provided with a long groove having a U-shaped section in a peripheral wall adjacent to a surface of the frame in contact with the lens.

6. The goggles according to claim 1, wherein the plurality of frame stop holes and the plurality of lens stop holes each consists of four holes.

7. The goggles according to claim 1, wherein each belt arm comprises a substantially squared U-shaped frame body having the bifurcated portions.

* * * * *